United States Patent [19]

Rericha

[11] Patent Number: 5,298,750
[45] Date of Patent: Mar. 29, 1994

[54] LASER PRECIPITATION SENSOR

[76] Inventor: Frank M. Rericha, 6270 Highway 61-67, Imperial, Mo. 63052

[21] Appl. No.: 821,422

[22] Filed: Jan. 15, 1992

[51] Int. Cl.⁵ .............. G01N 15/02; G01W 1/14; G06F 15/54
[52] U.S. Cl. .............................. 250/338.5; 250/353
[58] Field of Search ............. 250/338.5, 341, 343, 250/353, 574; 340/601, 602; 356/335, 436

[56] References Cited

U.S. PATENT DOCUMENTS

| 4,613,938 | 9/1986 | Hansen et al. ............ 356/336 X |
| 4,987,296 | 1/1991 | Kajioka et al. ............ 340/602 X |

FOREIGN PATENT DOCUMENTS

| 210676 | 2/1987 | European Pat. Off. ............ 356/436 |
| 58-143242 | 8/1983 | Japan ............ 250/338.5 |
| 61-231439 | 10/1986 | Japan ............ 340/602 |
| 2-300688 | 12/1990 | Japan ............ 356/436 |
| 1485069 | 6/1989 | U.S.S.R. ............ 356/335 |

*Primary Examiner*—Constantine Hannaher
*Assistant Examiner*—Edward J. Glick
*Attorney, Agent, or Firm*—Paul M. Denk

[57] ABSTRACT

A weather monitoring system comprising a laser precipitation sensor, including a housing, incorporating a bracket, for holding a prism or reflector means useful for deflecting the beam of laser light emitted from a transmitting diode, and for collimating said light and diverting it back into the housing for reception by a receptor diode, wherein the electronic components of the device including a microprocessor, RAM, ROM, and EEprom, all functioning in cooperation to provide an historical analysis and retention of data pertaining to the precipitation type, size, and intensity, of the precipitation that passes through the beam of laser light transmitted by the sensor.

10 Claims, 9 Drawing Sheets

LASER PRECIPITATION SENSOR

This invention relates generally to a weather monitoring system, and more specifically, it is designed to automatically identify and record the size and intensity of particles of naturally occurring precipitation within the atmosphere, and whether it be of any type of inclement weather, in the category of rain, mist, snow, and snow flurries. In addition, the concept of this invention is not only to record such data, but likewise to distinguish between the various types of precipitation involved, and to provide an instantaneous readout of information relative to the same.

BACKGROUND OF THE INVENTION

This invention provides a reliable sensor that combines the useful features of presently available related devices upon the market, but does so in a manner that substantially eliminates the inaccuracy generated by inferior features normally used in currently available devices. More specifically, the current invention utilizes a microprocessor based electronic circuitry, that is designed to record the size, intensity, and nature of the precipitation involved, and being encountered.

Generally, sensing devices currently available in the field of weather observation and monitoring all share one or more characteristics, and as a result, suffer in deficiencies or inaccuracies of detection, due to the effects of environmental conditions. Most of the currently available devices are contact devices, which suffer mechanical problems caused by the environment and the impurities generated and currently prevailing within the environment, at the time of gauging. Some of these earlier devices utilize destructive means to distinguish between the liquid and solid, such as whether water or ice precipitation is being gauged, and as to whether or not precipitation is in the liquid stage, or is generated through heat, evaporation, or artificial refrigeration. Many of these earlier devices utilize electrical properties in the category of resistance, capacitance, or inductance, to provide for their generation of a charge that is supposed to be detective of the type of environment being monitored. But, many of these devices have generally proven unreliable, due to many circumstances, but primarily due to the pollutants that exist in the atmosphere, which can cause changes in the electrical properties of the sensing means, depending upon the environmental conditions existing for that moment. Devices which employ any of the mechanical or electromechanical components normally used, have likewise proven to be generally unreliable, due to the elements of weather itself, and that is whether the environment is currently composed of wind, temperature, humidity, and atmospheric pressure, or their rapidly changing conditions. Lightning and elements of pollution also add to inaccuracy in the operations of the conventional monitoring devices.

Conventional instruments for monitoring atmospheric phenomenon use a number of different approaches. For example, various types of instruments are available that detect rain, mist, snow, snow flurries, frozen rain, and fog. Haze, dust and smoke are some of the other phenomenon in the atmosphere which can effect the efficient monitoring of these current type meteorlogical instruments.

One instrument available measures the rate and volume of liquid precipitation, and is known as the tipping bucket concept, which utilizes two reservoirs of known volume to collect the liquid precipitation, in its liquid state, and then have reporting intervals for monitoring when light or intermittent precipitation occurs. But, when wind effects come into play, the tipping bucket instrument may understate the actual rate and volume of the precipitation being generated by the atmosphere.

Another device for measuring volume of liquid precipitation employs the use of a collection chamber. This collection chamber empties itself via an orifice at the bottom of the chamber. The orifice causes water to form droplets which are theoretically of the same size, and are counted by optical or electrical means. Errors in volume reported can be caused by foreign matter intefering with the orifice, or having some effect upon the viscosity of the liquid involved.

Another device which employs the use of a conductive grid is used to indicate the pressence of a liquid precipitation. Corrosive elements in the atmosphere acting upon the exposed metal components of the conductance grid causes electrolysis which eventually deteriorates the grid or its electrical connections. This can lead towards deficient results.

A laser weather identifyer (LWI) is another means for sensing precipitation, and utilizing optical technology. The light source of the LWI consists of a gas filled HeNe laser modulated at a particular frequency. The receiver consists of three individually mounted optical detectors. All three of these optical detectors measure the amount of change of light present in their respective fields of view. Two of the detectors are mounted off-axis of the transmitted light source. The purpose of these two off-axis detectors is to detect forward scatter light difused as a result of a particle of precipitation passing through the sample volume. The LWI unit has several deficiencies inherent primarily due to the type of technology utilized in its design. False alarms due to vibration caused by strong winds or aircraft or automotive activity in the area affected can deplete the reliability of results obtained from this device. Strong vibrations induced into the instrument can cause a false signal to be indicated due to movement of the transmitter and receiver in different directions. This results in a change in the amount of light received by the detector. Furthermore, changes in ambient light can cause false readings. Direct or reflective light from any source radiation on the detector or detectors results in a change in the amount of apparent light measured from the light transmitter. Errors caused by multiple particles in the sample volume simultaneously can cause improper readings. When two or more particles are present in the sample volume simultaneously, the amount of light detected by the receiver is reduced, thus presenting an indication of particle size larger than the actual size of the individual particles present. The aforementioned multiple particles can effect the indicated velocity of the weather being detected. When two or more particles enter and leave the beam in succession there will likely be an indication that a single particle is moving at a slower velocity than it actually is.

High energy requirements, due to the use of an inert gas filled laser and the excessive quantity of parts in the integrated circuits to incorporate three receivers limits the possibility of mounting at remote sights. It is difficult to maintain four optical instruments in precise alignment in any harsh environment of the atmosphere, to provide satisfactory results from an LWI type of instrument. The physical size of the LWI unit, once again, limits the possible sights to which it can be mounted and used, primarily due to lack of available space. Meteorlogical stations are usually located in remote areas, employing tripods or towers. The large size of the LWI unit limits its usage on these types of supporting members. The mounting of a large instrument must be structurally sound due to the increased amount of wind resistance. Furthermore, some times this will dictate that the instrument be mounted at ground level, thereby reducing its sensitivity, and accuracy, in providing the type of concise readings required. Large, high visible instruments and remote locations are also likely to be targets of vandalism.

Earlier sensors that rely on changes and amplitude of light at the detector source are susceptible to accumulation of foreign matter upon the lenses, which can likewise cause errors in readings.

An example of earlier patented instruments utilized for weather observing is shown in the United States patent to Hansen, et al, U.S. Pat. No. 4,613,938, and entitled "Present Weather Observing System Utilizing Particulate Size and Velocity Measurements." This device provides a beam radiation in the atmosphere, including means having a field of view intersecting said beam to define a sample volume, for use for detecting scattered radiation from particles within the sample volume. From that, the size and velocity of at least one particle precipitating through the sample volume can be determined.

The United States patent to Chadwick, U.S. Pat. No. 3,487,684, is upon a precipitation measurement gauge. This particular measurement device is for use for monitoring the degree of precipitation in isolated areas. The device includes a precipitation-receiving vessel, a hydraulic-pressure responsive means connected to the vessel to respond to changes in the hydraulic pressure of precipitation received by the vessel, and a signaling means connected to the pressure responsive means. In its defined preferred form, a magnetic core is utilized, carried by a hydraulic bellows, that moves in and out of a stationary electric coil in proportion to the hydraulic pressure of the precipitation received by the vessel. Means are included to provide in circuit form having a coil to record or transmit signals in accordance with the position of the core in the coil.

SUMMARY OF THE INVENTION

A principal object of this invention is to provide a weather monitoring system, that incorporates a microprocessor based weather instrument, having a laser precipitation sensor therein, such that when the precisely controlled beam of collimated light is transmitted by the infrared means, and reflected by a prism, it provides a dual path for detecting the presence of precipitation, and through the cooperation of its microprocessor means, can provide for an accurate recording of the size and intensity of the precipitation involved, and distinguish between its type and through size characteristics, determine whether it he former of rain, mist, snow, snow flurries and sleet. In addition, the microprocessor can likewise determine the intensity of the environmental condition, as it prevails.

The advantages of utilizing the type of invention as defined herein, and which will be hereinafter analyzed, offers a variety of unique features, as follows:

1. It records, accumulates, and retains data of meteorological events.

2. It has serial ports for data transfer to and from a central processing unit.

3. It detects particles as small as 100 microns.

4. It has a beam which consists of a 3 mW laser diode with a gradiant index collimating lens.

5. It is capable of data transfer via radio frequency link or standard telephone line.

6. It has changeable software for different applications.

7. It measures particle size, regardless of the type of particles involved.

8. It calculates the intensity of the environment, such as for providing an indication as to the intensity of the storm involved, calculates this intensity, for providing a readout of data relative to and more specifically interpretive of the type of and severity of storm encountered.

It is an object of this invention to provide an improved laser precipitation sensor for identifying a wide variety of types of precipitation.

It is a further object of this invention to provide a laser precipitation sensor that utilizes a mininum number of components, uses a minimum of energy, is compact in size, and as result, is far less susceptible to malfunctioning, or deterioration.

It is another object of this invention to provide a sensor for determining size and velocity of particles of precipitation.

It is yet another object of this invention to provide a sensor for distinguishing between particles of precipitation and other suspended particles present within the atmosphere.

It is yet another object of this invention to instantly identify any incipient and termination of the event of precipitation. In other words, this device simply lets you know when the storm starts, and when it ends.

It is still a further object of this invention to provide an advanced laser precipitation sensor having no false reading characteristics, such as normally may be caused by wind, dew, frost, vibration, interference, or radiation present within the atmosphere.

Still another object of this invention is to provide an improved laser precipitation sensor for establishing the volume of precipitation encountered.

Yet another object of this invention is to provide such a sensor to measure the volume of individual particles of precipitation present.

Still another object of this invention is to delineate between various types of precipitation that may be present, and identify it as either rain, mist, snow, or snow flurries.

Still another object of this invention is to provide an instrument which records, accumulates, and retains meteorological data for later retrieval and usage.

This invention contemplates the incorporation of means for providing a beam of collimated light, within the instrument, and further incorporating means for detecting the interruption of said beam due to the passage of precipitating particles therethrough. In addition, the instrument incorporates microprocessor for determining the type of precipitation through its recording of the size and velocity of the particles passing through the sample volume gauged by the capacity of the beam of collimated light. The invention further includes means for determining the size and velocity of the precipitating particles by recording the interval during which the beam is interrupted, which is directly proportional or related to the size and rate of the free falling decent of the particle being identified. The identification means includes means for accumulating information relative to groups of such particles of precipitation, and matching this detected information to predetermined values of size and velocity, that may be incorporated within look-up tables provided within the microprocessor. The invention further includes means for ascertaining the volume of precipitating particles, and means for summing the volume of more than one particle within a known period of time.

The invention further includes means for modulating the infrared light utilized within the sensor, and in the preferred embodiment, utilizes infrared light in a square wave pattern and more specifically at 38.4 kHz. The invention further includes means for detecting the modulated light at said frequency. The invention further includes means to provide a folded beam path, or one which may be deflected, to provide infrared light of parallel beams, thereby keeping all of the electronic components of the light source and detector within one confined area, or its housing means, which facilitates its servicing, and reduces the potential for its deterioration. Utilizing this particular concept effectively doubles the sensing area, without increasing the size of the instrument involved. In fact, it is likely that further prism means could be utilized to provide for multiple paths of reflection of the light into, preferably, parallel paths, for furnishing information read-out, detection, analysis, and evaluation, by the microprocessor. In the preferred embodiment, this infrared light is folded or deflected by means of mirrored prism. This invention further includes a 3 mW laser collimated at 3.3 × 1 mm, and radiated at a detector through an aperture of 100 microns in diameter. This results in a most favorable signal to noise ratio.

This invention further includes means for accumulating, retaining, and the retrieval of recorded information concerning events transpiring during the occurrence of precipitation, to provide for its detection. The invention further includes a series of ports, or serial ports, for means of digital communication to another processor, or to any other destination. The invention further includes an automatic radio keying device to provide for communication via radio frequency. This sensor incorporates means for detecting various factors which would otherwise result in a deterioration of factural information from the instrument, in order to maintain its proper operations. The invention further includes means for monitoring the proper execution of the program code, within the microprocessor, to furnish a status of the VCC (5+VDC) signal and provide a guaranteed reset signal. It includes the ability of its processor to receive, store, and alter commands in non-volatile memory. This is achieved through the usage of an electronically erasable program read only memory device, generally identified as an EEprom.

This invention further includes means for recording the actual date and time of each event of precipitation. It also mathematically provides information on the average size of the particles or precipitation detected. It detects and records a number of particles of precipitation for a period of time, such as per second. It includes a microprocessor for receiving and processing information from external temperature, relative humidity, and wind speed/direction sensors for use in the algorithm of determining the types of precipitation involved.

It is believed that precipitation measurement technology has been heightened through the usage of the structure of the device of this invention. It offers distinct electrical and mechanical advantages over standard precipitation sensors. The laser sensor of this invention is used in applications where performance must be done highly efficiently, since calculated values of high accuracy just cannot be compromised, since such information may be required for highly sensitive operations, such as used in conjunction with airline operations, etc. Unique pulse infrared laser and microprocessor design means of this invention provides accurate faster measurements, a reduction in false alarms, and the flexibility to interface with other computers, even at a remote location. Custom designs or variations of standards can he built into this device to meet specific requirements, and to provide the right solution for the system design needs, depending upon the area of employment. These important features, along with the ability of this sensor to measure and count particle size, distinguish between snow and rain, and to indicate storm intensity, all done within a compact unit and packaging, and operating at high reliability, is believed to provide uniqueness that advances the state of this art.

Additional key features of this invention include its application of a high performance pulsed laser, manipulated into a folded, dual, or multibeam path, it is microprocesser based, and through the use of its memory, can store historical data relative to environmental conditions encountered over a long period of time. The specific storm intensity factor can be determined, in addition to the type of storm involved. While it is electrical or electronically operated, it likewise can be battery functioned, or even solar powered. It has overange indication, and can measure and count the particles involved, and readily distinguish between the liquid or solid precipitation stages encountered.

Other objects, features, and advantages inherent from the structure and principle of operation of the laser precipitation sensor of this invention will derive from the following description of the invention provided herein in view of its accompanying drawings.

DESCRIPTION OF THE PREFERRED EMBODIMENT

Figures 1, 2:
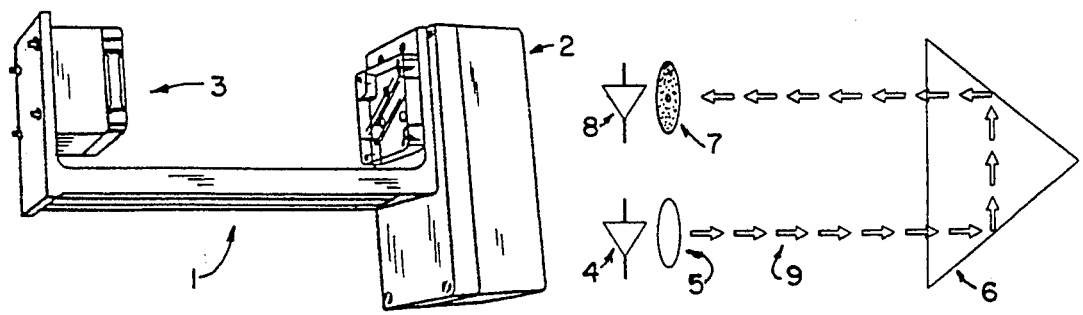
FIG. 1 is an isometric view of the laser precipitation sensor of this invention.
FIG. 2 is a schematic plan view of the infrared beam source, its diversion, and detector.

The laser precipitation sensor of this invention is shown in FIG. 1, and which generally includes a bracket 1 for supporting the optical components of this development, and which bracket may be formed of aluminum, metal, wood, but preferably of weather resistant materials that will not oxidize, etc. Generally, the source of the infrared laser, or other light means, is embodied within the electronic component casing or housing means 2, mounting the bracket, or supported upon the bracket, at one end, as noted, while at the opposite end of the bracket, which may be upturned as shown, there is provided a weather tight or hermetically sealed enclosure for holding the mirrored prism, as at 3. FIG. 2 shows, schematically, the path of the infrared light that is emitted from the source 4, and generally a right angled prism, as noted at 6, is used to fold or deflect the beam back into a parallel path, of collimated light, which is advantageously used within the operations of this particular development, for reasons as previously summarized, and as to be described herein.

All of the electronic components of this sensor are mounted within a single, radio frequency interference shielded enclosure 2, as noted, as can be seen in FIG. 1. The folding and collimating of its beam effectively doubles the sensing area of the sensor, without increasing the size of the instrument involved. Furthermore, by constructing the unit in this manner, it simplifies the alignment of the optical components of this sensor. In addition, the utility of this instrument is maximized due to its reduced size, and ease of mounting, much less facilitating its servicing, when necessary.

The source of light energy, or light transmitting means, is generally in the infrared category, and in the preferred embodiment, is maintained at a 3 milliwatt laser (mW) diode, as at 4, as disclosed in FIG. 2. The diode radiates its energy through its lens 5, which effectivley achieves a collimating of the light beam, and preferably within a wavelength of approximately 810 nanometers (nm). The light is then conditioned by the lens 5, and the lens radiates its collimated beam 3.3 x mm in diameter with a beam divergence of less than 2 micromillirads (MRAD). The beam 9 is then directed at the prism 6, which as previously explained, in the preferred embodiment, is a right angled glass prism, although other angles of deflection may be utilized, even nonparallel, such as derived from a flat mirror deflector. The prism is often "preferably" constructed as an incline mirror, so that in application it can withstand any severe acoustics or inertial loads, because of its facility to mount, and to be subjected to less deformation than a regular mirror in response to external mechanical stress. The prism or mirror is mounted in a polycarbonate watertight enclosure, as noted at 3, in FIG. 1, in order to protect and enhance its reflective coatings. The prism mounting, which can be adjusted, consists of a tripod arrangement, not shown, which enables the beam to be aimed at the detector 8, as to be described.

The detector 8 consists of a photodiode 8, as noted in FIG. 2, and which has a spectral frequency range of 400-1100 nm, a responsivity of 0.41 A/W at 830 nm, an active area of 31 mm sq. and leakage current of 31 nA. The detector has a field of view which is determined by the aperture 7, as noted. This aperture is formed within a stainless steel disc with a substrate thickness of approximately 0.013 mm, in the preferred embodiment. The focusing aperture hole is precision laser-drilled, and is completely free from any defects normally seen in pinholes prepared by vacuum deposition, dielectric substrates, or by mechanical means. The aperture is exceptionally round and free of any edge distortion, so as to allow a precise collimated light beam through to the detector, free from any peripheral distortions.

This invention in the preferred embodiment is designed to use an aperture of 100 microns, however, apertures of different diameters may be utilized with this instrument to detect other elements.

The purpose of the apertured disc and its application within this sensor is to provide a highly controlled beam of collimated light to be received by the detector, and because it is of a precision dimension, and of minuscule diameter, it is the blockage of this light beam by the precipitation that is passing therethrough, as the collimated light is transmitted, deflected, and then returned to the detector, that is gauged for determining the existence and type of precipitation involved, in addition to its quantity. All previous precipitation sensing means operate upon a different principle comprising the change in amplitude of the sensed light, meaning that there is always some light that gets through to its detector, rather than operating off of the principle of blockage of the light, as a means for determining and detecting the precipitation encountered.

The sample volume is defined as the amount of space occupied by the area of the aperture times the distance of the exposed beam path, as it passes in its collimated condition between the sensor and the deflector prism.

The laser light source projects a beam of collimated light at the $3.3 \times 1$ mm dimensions towards the stainless steel disc having its aperture of 100 microns formed therethrough. The only amount of light utilized to detect particles of precipitation is that which passes through the 100 micron aperture. Therefore, the instrument utilizes a column of light 100 microns in diameter, or width, with the particles of precipitation being detected passing through and momentarily blocking this column of light.

Figure 8:
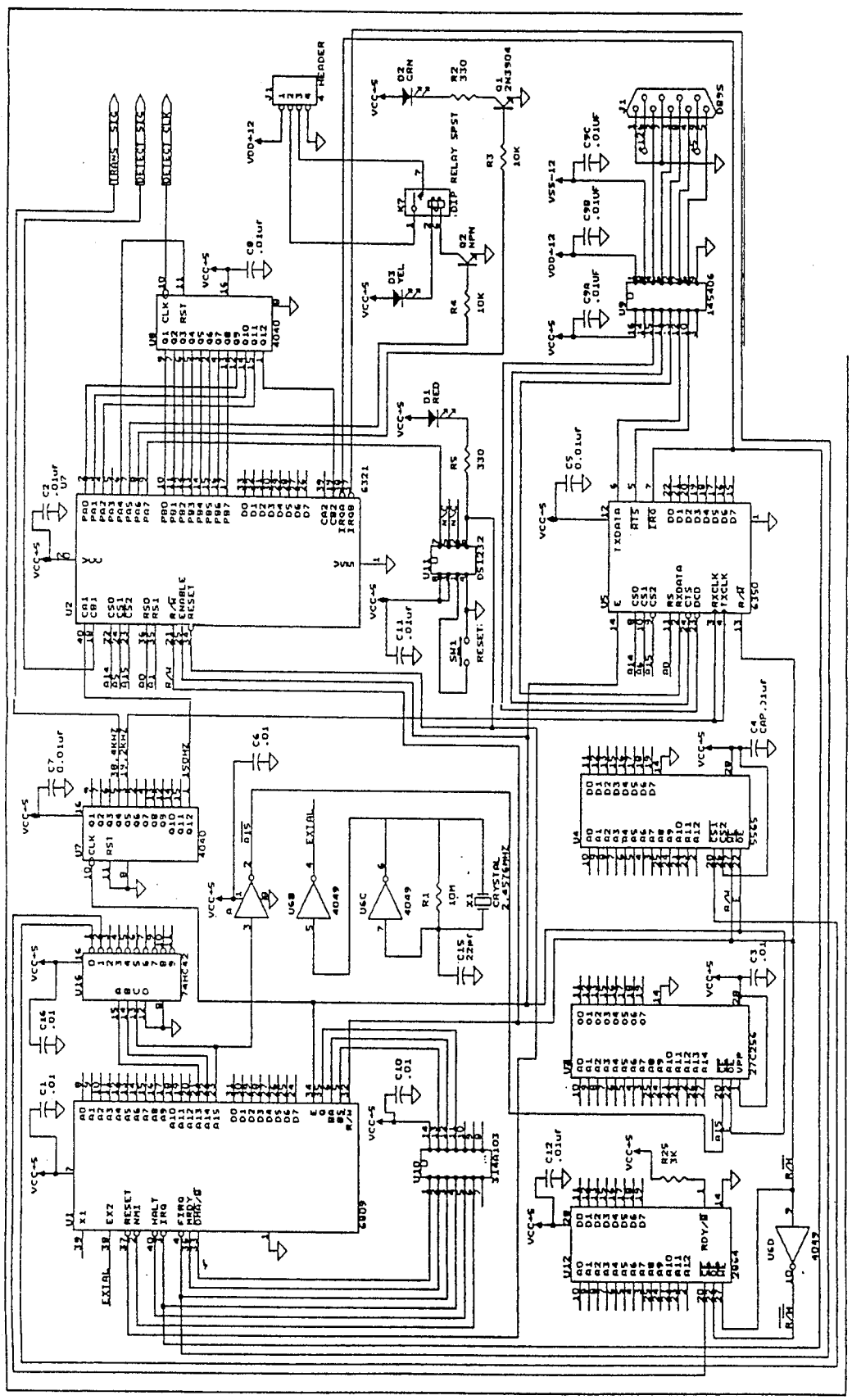
FIG. 8 is a schematic illustration of the electronics of the digital microprocessor circuitry of this invention.

The essence of the sensor of this invention is a high-performance 8-byte Motorola processor, generally available under code No. MC63B09, from the Motorola Company, of Chicago, Ill. FIG. 8 discloses the structure, circuitry-wise, of this microprocessor, and which generally functions at a frequency of 2.4576 mHz. Its oscillator consists of two inverting buffers, U6B and U6C, a resistor R1, a capacitor C15, and one crystal X1.

Figure 9:
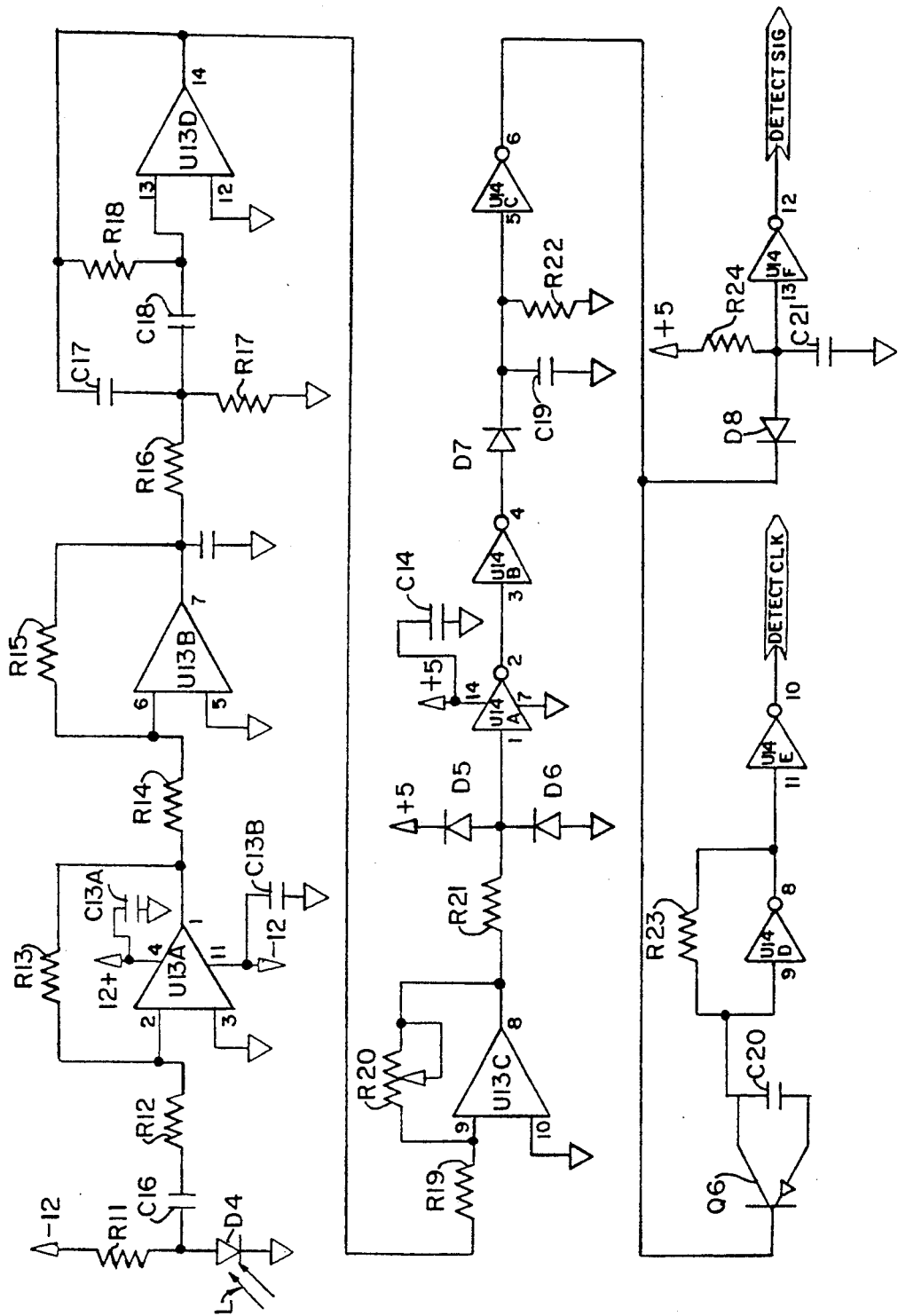
FIG. 9 is an electrical schematic illustrating the receiver-amplifier circuitry.

FIG. 8 provides the overall circuit diagram and the component assembly for the precipitation processor or microprocessor of this invention. On the other hand, FIG. 9 provides the means for conversion of the light beam, as received by the detector, from a light signal into an electrical signal, that can be processed by the microprocessor. For example, the light signals L, as can be seen in FIG. 9, are received by the detector D4, which corresponds to the diode 8, as previously explained in FIG. 2, wherein the light signals are converted into an electrical signal, for further processing. The operational amplifiers U13A and U13B amplify the signal received, which is then filtered by the band pass filter U13D, and then an adjustable gain amplifier U13C provides for further amplification, with the signal as outputted therefrom then being processed by the inverting buffer U14A, in combination with the diodes D5 and D6, which convert the signal into the TTL logic, providing for the output of signals in a range of 0 to 5 volts, and which signals are then processed by the Peek detector, formed by the diode D7, the capacitor C19, the resistor R22, and the inverting buffer U14C, as noted. At this point, the signal is representative of the existence, or not, of a particle of precipitation within the light beam of the sensor. The detector clock, as noted, provides an indication as the length of time that a particle is present within the light beam, and its signal is processed by the transistor Q6, its capacitor C20, resistor R23, and the inverting buffer U14D. The inverting buffer U14E provides for a transformation of the signal into the proper polarity, for providing a readout of the detect clock for determining the length of time that a particle is within the light beam. In addition, the Peek detector, as previously explained, after the particle leaves the light beam, provides its circuitry to interupt the microprocessor and forces the subroutine of the precipitation processor, of FIG. 8, to read the information outputted from the detect clock, to determine other characteristics regarding the precipitation encountered, as will be subsequently defined, for determining also its type, intensity, in addition to the length of time that it was present. Its signal is outputted by the detect signal, as noted.

Figure 10:
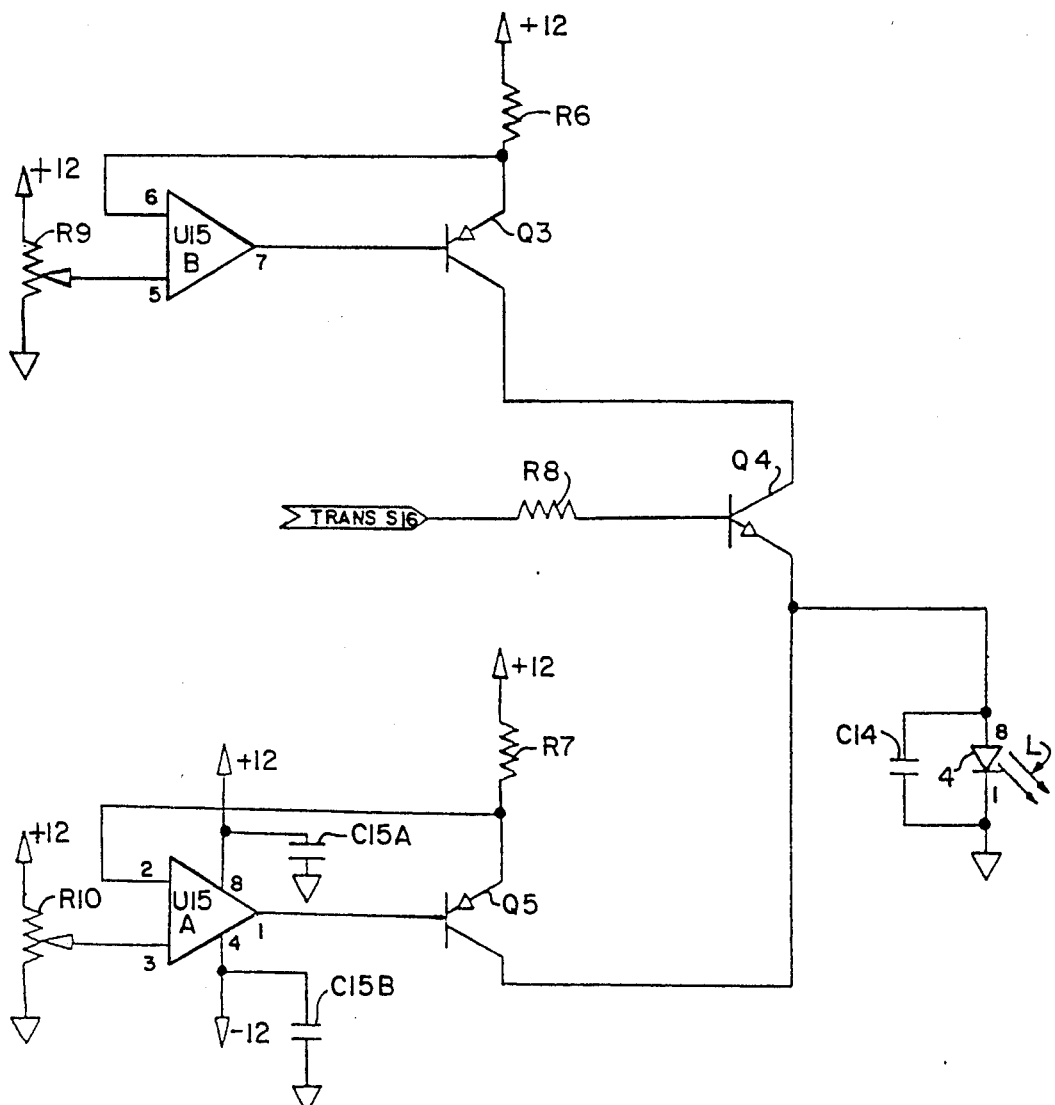
FIG. 10 is an electrical schematic illustrating the constant current power supply for the infrared laser diode of the sensor of this invention.

The signals received by the microprocessor, as can be seen in FIG. 8, provides for inputting of the detect clock signal, in addition to the detect SIG, where noted. Furthermore, there is a transmission signal, identified as TRANS SIG, which is a signal that is maintained generally at 38.4 kilohertz, in the preferred embodiment, and this particular signal, as can be noted, is derived from pin 5 of the clock U7, as noted. This particular signal, as to be subsequently described, and as noted in FIG. 10, is conducted to the power supply circuitry, and which provides for a frequency of operation of the modulated light beam delivered from the transmitting means 4, comprising the transmitting diode as previously explained. This circuitry will be subsequently analyzed, as set forth in FIG. 10.

In FIG. 8, though, the main microprocessor chip is U1, and this particular microprocessor, as previously explained, controls the functional and electronic operations of the sensor, during is functioning. This provides for this sequence of operations of the device, during usage. The actual software or program for the device is embodied upon the ROM U3, and which instructs the processor which sequence of operations to perform, and what subroutines to initiate. The RAM U4 provides for a storage of the history of the precipitation encountered, and presently, information relating to 256 particles of preciptiation may be stored in this RAM for use for providing an anlysis of the type of precipitation encountered. U12 is an EEprom, and in this particular instance provides for a storing of set-up commands for providing set points for, for example, temperature and relative humidity detection, or for receiving remote communication commands from other sources. The communications chip U5 provides for serial communication, which allows for communication between other modems, data buses, or the like, for the transmission of calculated data regarding the precipitation to other central processors, such as CPU, or the like. At that point, the information received by the CPU may be further processed by a personal computer, or other computing means. The chip U9 comprises a converter, and which converts the signal from TTL to RS232, which is a standard output signal for transmission, with the signal then passing through the connector J1, as noted, for conducting to other sources, such as a CPU. The chip U8 is a ripple counter, and which converts the detect clock signal from a serial to a parallel format, for delivery of the signal to the peripheral interface adaptor U2, wherein the clock signal is processed, and provides for the transmission of the clock signal from the detect clock, as explained in FIG. 9, to the data bus, as noted at the chip contact point D0 through D7, as can be seen through the circuit. The address decoder U16 provides for memory mapping of the various chips or components provided within the microprocessorly to provide for their proper sequence of operations, and to have them properly addressed, for functioning.

A twelve stage ripple counter or clock, U7, incorporating a pin 10 clock input is connected to the "E" signal generated by the processor. This ripple counter generates timing signals for the real time clock, and the transmit/receive rate for the 6850 ACIA serial communications port and modulation frequency of the laser. The microprocessor includes an 8K EEprom, U12, as aforesaid, which is used to store various user programmable set-up information such as modem set-up commands, temperature/relative-humidity set points, and radio or telephone communication commands. An 8K RAM, U4, is employed extensively by the microprocessor, and it stores accumulative data regarding the precipitation being sensed. A 32K ROM, U3, has various inherent programs, and subroutines and directories, which allows for the flexibility of different applications by the change of one programmable integrated circuit. And a synchronous communication's interface adaptor (ACIA), U5, provides the data formatting and control to interface serial asynchronous data communications to the data bus. All serial communication within the microprocessor is handled through the interrupt request signal (IRQ).

Figure 7:
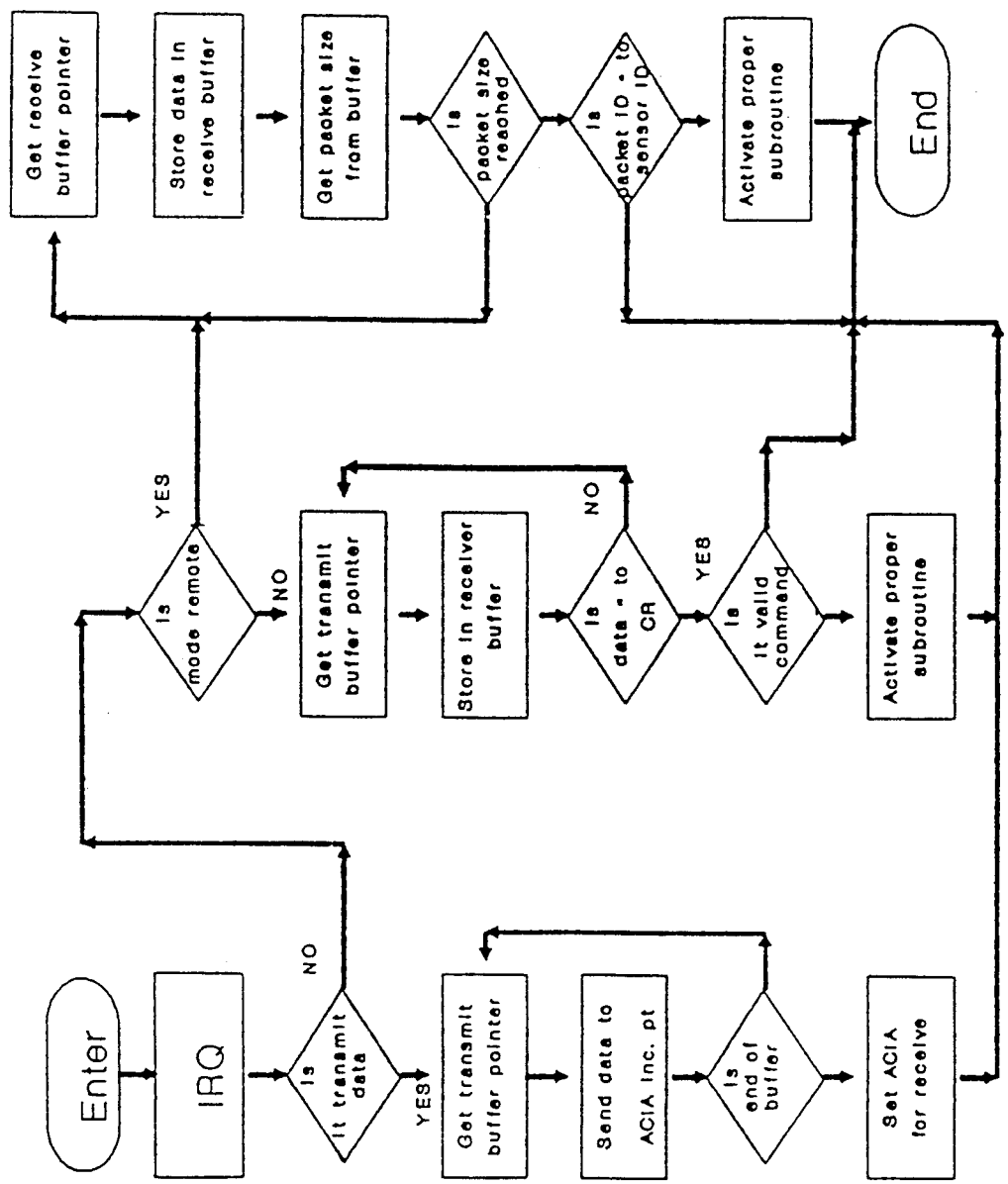
FIG. 7 is a flow chart of the input/output subroutine of the microprocessor of the sensor of this invention.

FIG. 7, as previously explained, provides a flow chart of the input/output subroutines showing the response to the interupt request signals received from ACIA. A line driver, U9, is an RS-232 line driver, and is used to interface between the ACIA TTL signal, and the RS-232 standards.

Figure 3:
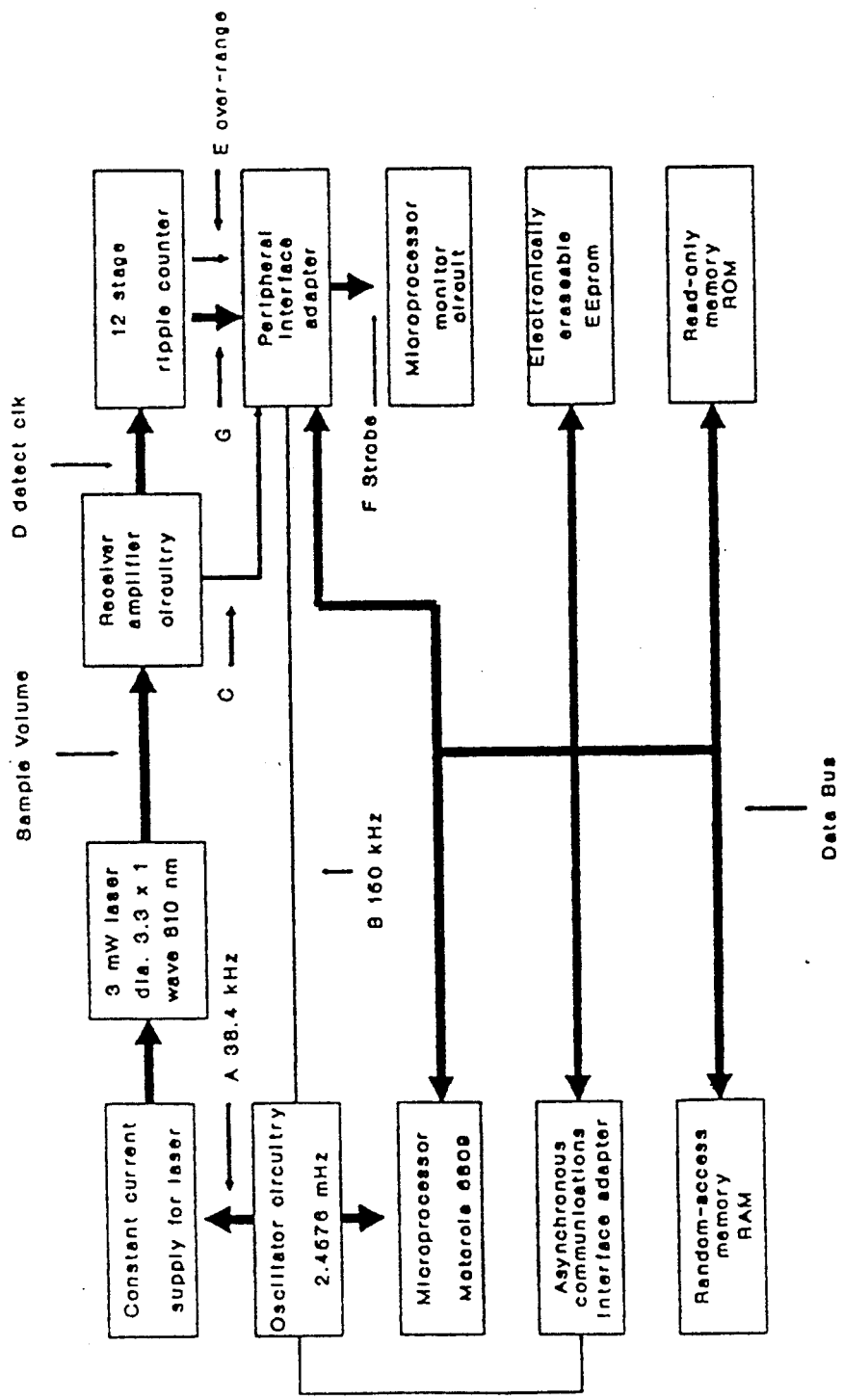
FIG. 3 is a block diagram of the electrical signal processing as performed by the sensor of this invention.

The components set forth in FIG. 8, and identified as U11, is a precision temperature compensated reference and comparator circuit, that is used to monitor the status of the VCC. It monitors three of the vital conditions for the microprocessor. When an out-of-tolerance condition occurs in the VCC below 4.5 volts, an internal power fail signal is generated which forces reset to the active state. When the VCC returns to an in-tolerance condition the reset signals are kept in the active state for a minimum of 250 ms to allow the power supply and processor to stabilize. The second function of U11 is to provide a push button reset control, it debounces the push button input and guarantees an active reset pulse width of 250 ms minimum. The third furnction is a watch dog timer which forces the reset signal to the active state if the strobe input of FIG. 3, signal F is not driven low prior to time out. The strobe is produced through software control of a peripheral data line U2, as disclosed at pin 9 in FIG. 8. When a microprocessor is functioning normally, the signals would as a matter of routine, cause the CMOS microprocessor monitor circuit to be reset prior to time out. This halts and restarts an out-of-control microprocessor.

Figure 6:
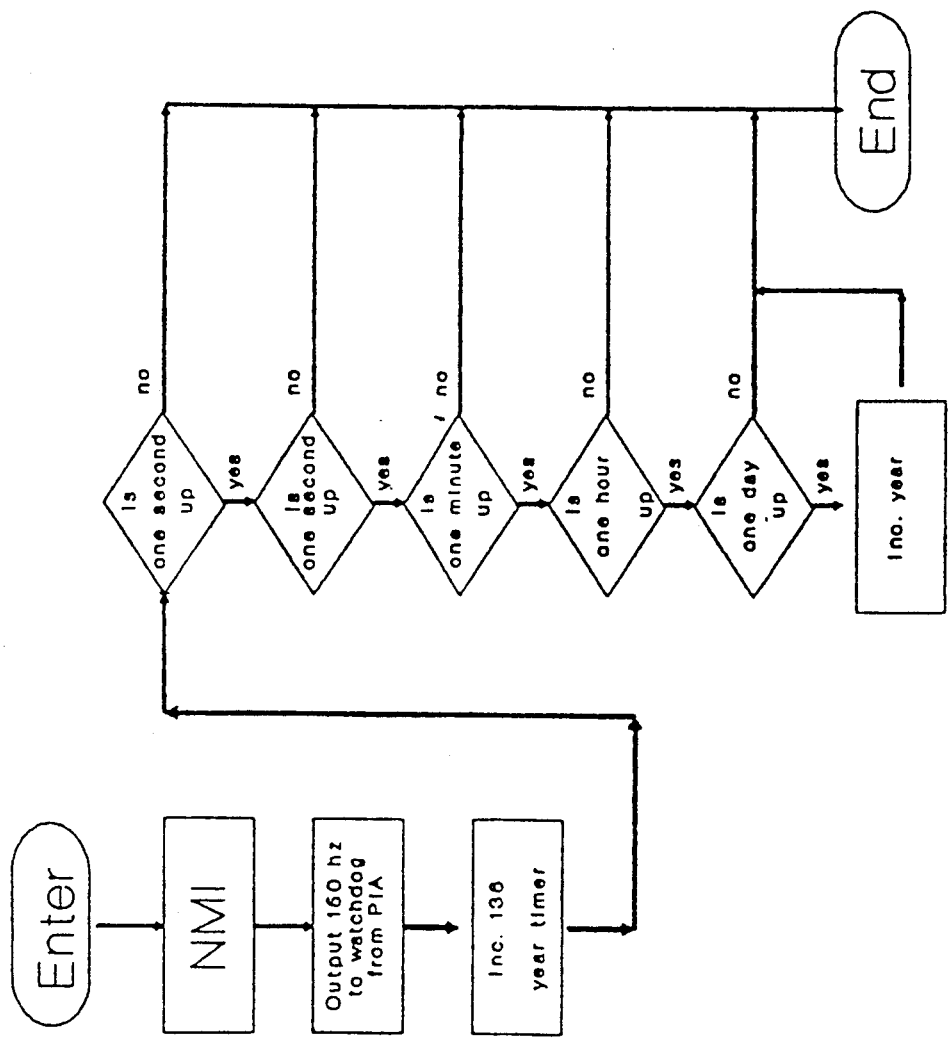
FIG. 6 is a flow chart of the real time clock subroutine of the microprocessor of this sensor.

Component U2 of the device, as disclosed in FIG. 8, is a peripheral interface adaptor PIA which has several interface functions. The first function is to accept a 150 Hz signal into the CA1 from U7, its pin 1, which is used to activate a nonmaskable interupt for a real time clock and a 136 year timer, as disclosed in FIG. 6, in addition to FIG. 3, as signal B. Each time this interupt signal is received, it causes the program to execute subroutines that update the clock and timer. The second function is a visual aid which is a green LED and transistor connected to data line pin 8. This LED is switched on for 50 ms when a valid particle is detected. The third function is to control a relay which can be used to key a radio transmitter or as a Yes/No analog output, depending upon the mode of operation. This circuit consists of a transistor, a relay, and a yellow LED which is connected to a data line pin 7. U15, Q3, Q4, and Q5, all as disclosed in FIG. 8, and other associated components, as shown in FIG. 10, constitute a constant current power supply for the laser diode. The power supply consists of an adjustable low current supply and an adjustable high current supply. The current through the laser diode is switched between high and low current by Q4, which is driven by U7, pin 5, at 38.4 kHz.

Components U13 and U14, and associated components as disclosed in FIG. 9, constitute the detector circuit for the laser beam. The laser signal is detected by photodiode D4, and coupled to U13A through C16. U13A is configured as an inverting amplifier with a gain of 1000. The signal is then directly coupled through R14 to U13B which is an inverting amplifier with a gain of 22. It is then subjected to a band pass, multiple feedback filter with a band pass of 5 kHz, a center frequency of 38.4 kHz, and a Q of 7.6. This circuit consists of U13D C17, C18, R16, R17, and R18. U13C is configured as an inverting amplifier with a variable gain from unity gain to a gain of 10. Next, the signal is converted into TTL levels by diodes D5 and D6, and squared by U14A, and inverting Schmitt trigger. U14B is used as an inverter so the proper signal polarity enters the Peek detector which consists of U14C, D7, C19, and R22. With a loss of signal into the detector circuit, the Peek detector will change the output of U14C. From here the signal splits and goes to an oscillator and a pulse stretcher. The pulse stretcher consists of U14F, D8, C21, and R24. The purpose of this circuit is to stretch the signal generated by the Peek detector allowing the oscillator to stablize before interrupting the microprocessor to take a reading. This circuit also prevents any unwanted noise spikes from interrupting the microprocessor. This stretched signal is connected to U2, pin 18, CB1, FIG. 1, FIG. 3, signal C. This signal is called detect signal. The oscillator circuit FIG. 9 consists of U14D, Q6, C20, and R23. When the Peek detector changes status, Q6 switches off activating the oscillator. The signal is then squared by U14E. This signal is called detector CLK which is connected to U8, pin 10, FIG. 8, FIG. 3, signal D. Component UB is a 12-stage ripple counter which converts the detect CLK into a binary output FIG. 3, signal G, for the PIA to read. The miroporcessor takes this reading when it receives the detect signal. After taking a reading, the microprocessor clears U8 to a low level by applying a logic high on the reset pin. This is done with the PIA data component U2, pin 6, to U8 pin 11. Component U8 pin 1 is connected to U2 pin 19 which is CB2, FIG. 3, signal E. This interrupts the microrocessor when the ripple counter wraps around.

As previously briefly referred to, the transmission signal that is used to provide for frequency of operations of the light signal delivered to the instrument, by way of its light transmitting diode 4, as previously explained, is shown in FIG. 10. The incoming signal, TRANS SIG, passes through a biasing resistance R8, for its delivery to the base of the transistor Q4, which provides for a switching on and off of the signal, to furnish it with its frequency of operation. This particular signal, as delivered, is preferably cycled within a range of operation, and as can be seen, there are upper and lower levels of intensity, which is dictated by the constant current regulator, which includes the operational amplifier U15B, and which has its intensity of operation, and more specifically its voltage level, established by means of the potentiometer R9. Generally, in the preferred embodiment, it is established at an upper level of amperage intensity, for the signal generated, set at approximately 60 milliamps of operation. On the other hand, the lower generated signal is established by means of the operational amplifier U15A, and which is set by its potentiometer R10, to generate a signal in the range of 30 miliamps output. Thus, the frequency of operations of the transmission signal, when it generates and transmits a signal to its light transmitting diode 8 (FIG. 2), is between the range of 30 milliamps and 90 milliamps, in the frequency of the light signal generated by means of the diode 4, as previously explained. The light L generated therefrom is that light which is passed along the light beam 9, and collimated, deflected, and it is through this light beam that the precipitation enters and passes, to provide for its detection, and then a determination of its type, and intensity, by means of the circuitry as previously explained in FIGS. 8 and 9.

Figure 4:
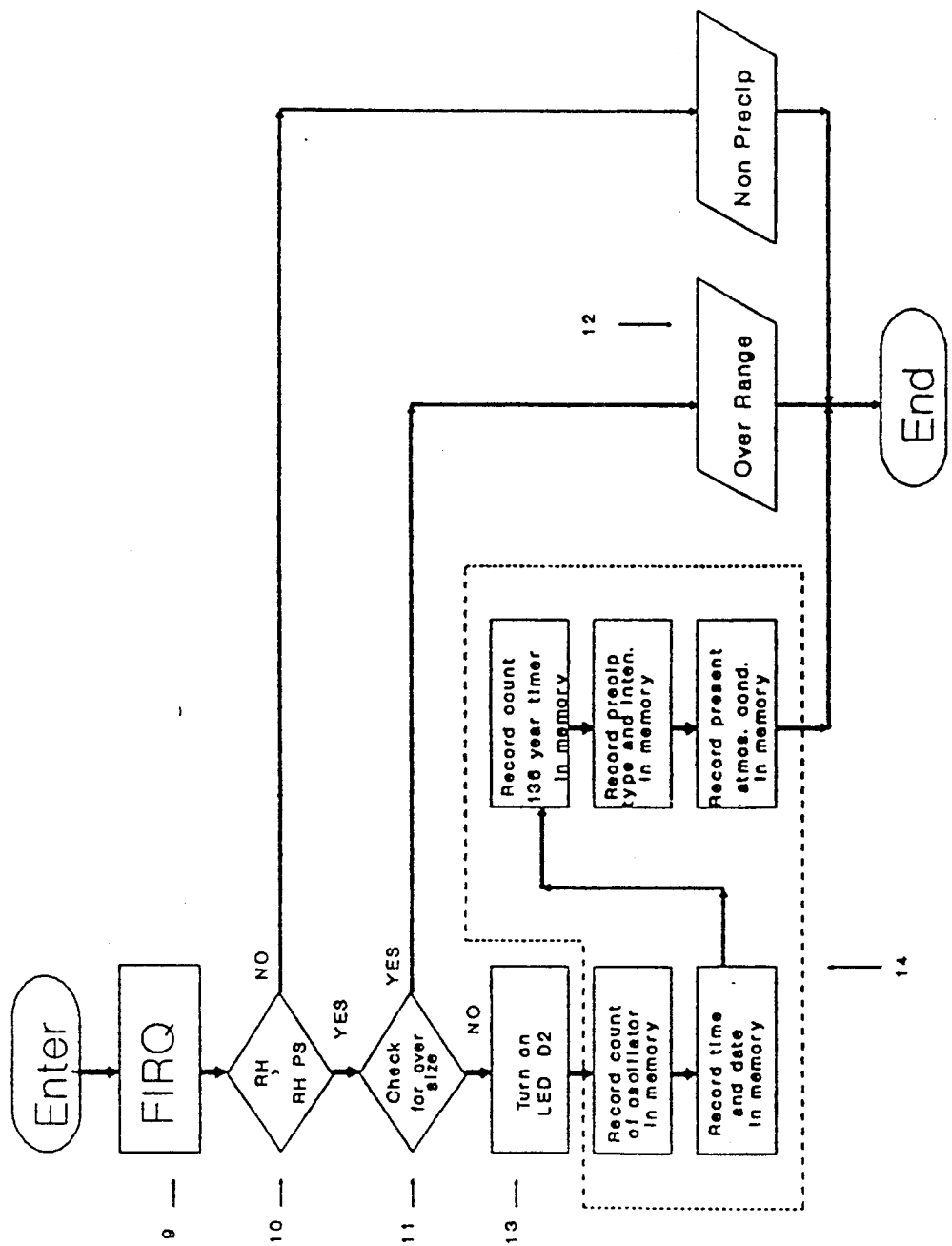
FIG. 4 is a flow chart showing the response of the sensor to a particle passing through the sample volume.

FIG. 4 is a flow chart of the response to the fast interrupt request (FIRQ), as noted at 9. FIRQ initiates the retrieval of information from the detector circuit, of FIG. 9. This subrouting then compares the current relative humidity reading to the relative humidity set point 10. The current relative humidity value must be greater than the relative humidity set point to indicate precipitation as at 10. The next function is a check to determine if a twelve stage ripple counter U8 has overflowed, as at 11. If this occurs, the determination is that the particle is larger than a particle of precipitation. If it did not overflow, the indication is that precipitation is present. This is a safeguard in the event of loss of the signal, which may be indicative of the presence of unauthorized obstructions, such as a failure of laser, presence of a birds nest or a spider or the like. If loss of signal is permanent, microprocessor will indicate a malfunction, as at 12. When valid precipitation has been determined, LED D2 (FIG. 8) is switched on at 13. This LED is a visual aid for technicians only to use or observe. The information following is recorded in packet form, as at 14, for each valid particle of precipitation. This oscillator count which represents the amount of time the particle was in the sample volume, the time and date stamp, the 136 year timer count, the present precipitation type, the present precipitation intensity, and the present atmospheric conditions are all stored in memory, such as the RAM U4.

Figure 5:
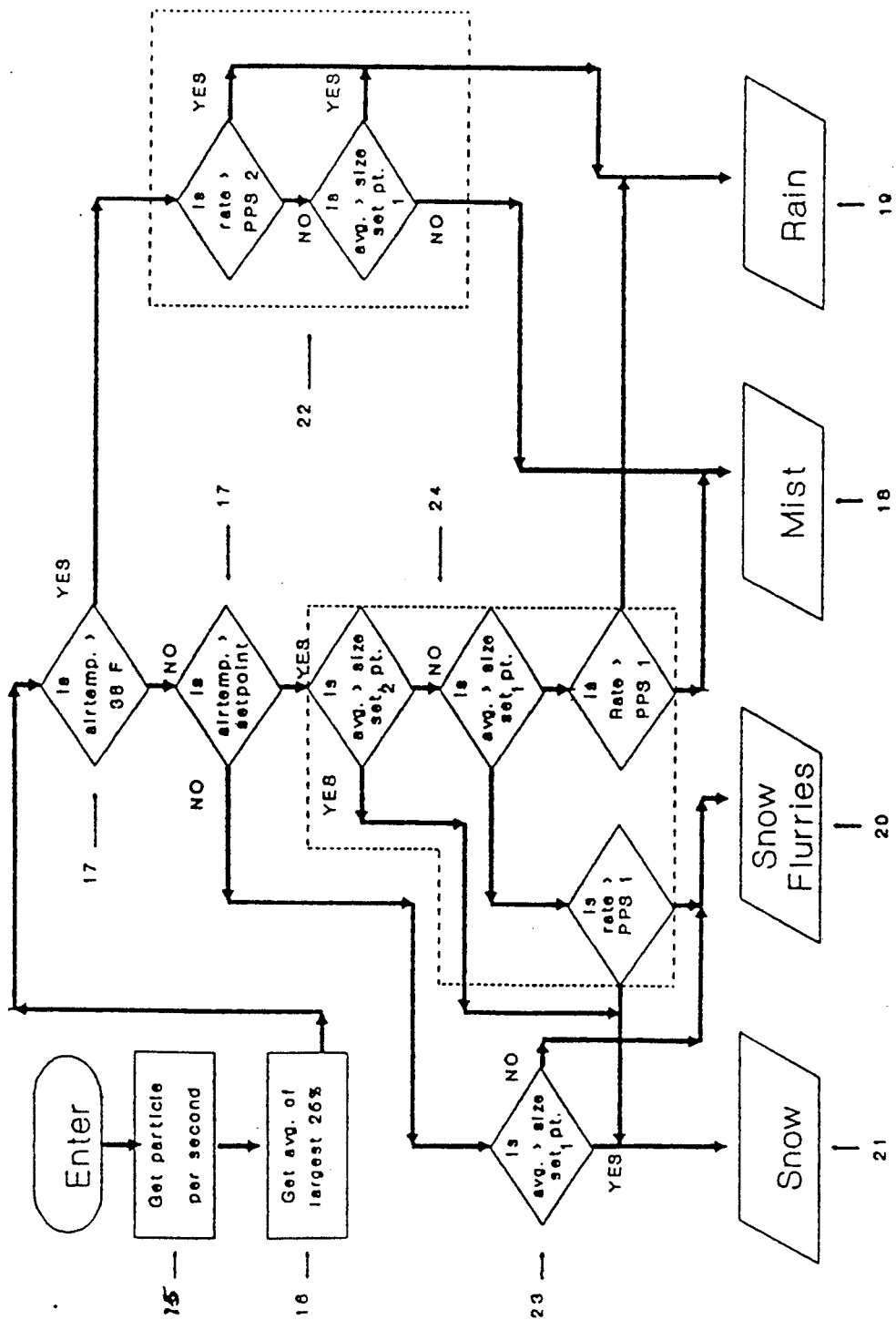
FIG. 5 is flow chart of the precipitation identification routine of the sensor.

FIG. 5 is a flow chart for determining types of particles of precipitation through a series of comparisons and calculations to determine the quality of precipitation, as a further subroutine provided in the ROM U3.

Figure 11:
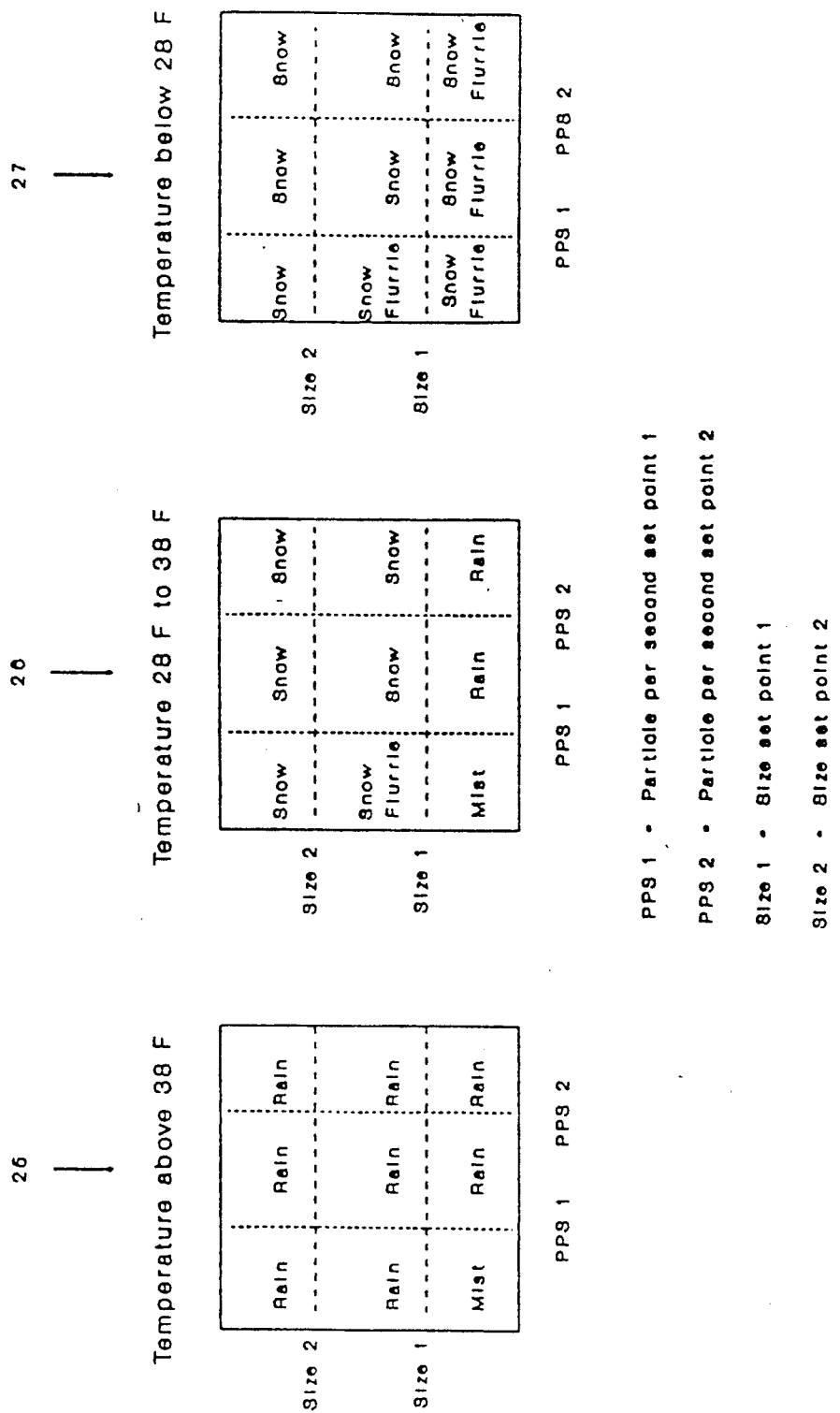
FIG. 11 is the cross tab illustration of the three possible algorithms for detecting the type of precipitation encountered by the sensor during application.

Three parameters are followed here. First is average particle size, FIG. 5, as noted at 16. The second is particles per second, or the rate detected, as determined at 15. The third is the air temperature. The air temperature determines which algorithm, as at 17, is used. At an air temperature above 38° F., the program selects, as at 22, the precipitation types of either mist, as determined at 18, or rain, as determined at 19, as can he noted in FIG. 11, as at 25. At air temperatures between the air temperature set point, and 38° F., as noted at 24, the program selects one of the four types of precipitation, as set forth in FIG. 11, as at 26. Each algorithm in this flow chart uses common set points. Also, determining the type of snow is programmed for detection, as noted at 27 in FIG. 11. There are two different size set points, and two different rate set points. This leads to a possible choice of any one of nine different circumstances per algorithm.

Variations or modifications in the subject matter of this invention may occur to those skilled in the art upon reviewing the subject matter of this invention. Such variations, if within the spirit of this invention, are intended to be encompassed within the scope of any claims to patent protection issuing upon this development. The description of the preferred embodiment set forth herein is done so for illustrative purposes only.

Having thus described the invention, what is claimed and desired to be secured by Letters Patent is:

1. A laser precipitation sensor for detecting precipitation and for determining its type, whether it be a determination that the precipitation is rain, mist, snow, or snow flurries, and its intensity, said sensor including: a housing means, a light transmitting means embodies in said housing means and provided for transmitting a beam of light, light deflector means disposed a spaced distance from said light transmitting means and provided for deflecting said light beam, said light deflector means comprising a prism, structure means disposing said light deflector means said spaced distance from said light transmitting means, a bracket, said bracket connecting to said housing means at one end and said bracket connecting to said structure means at its other end, said bracket providing for said spaced distance between the light deflector means and the light transmitting means so that precipitation falling intermediate said light transmitting means and said light deflector means and interrupting said light beam is detected, said deflector means in combination with said light transmitting means providing for deflecting of said light beam and directing it back into said housing means, the deflected light beam being parallel to said transmitted light beam, thereby providing a pair of light beams for detecting the precipitation, a light receiving means provided in said housing means for reception of the interrupted light beam, said light transmitting means comprising a laser diode, and said light receiving means comprising a photo diode, both said laser diode and said photo diode being contained within said housing means, a microprocessor means also contained in said housing means and in combination with said light receiving means, said light receiving means providing for a conversion of the detected light beam into electrical signals, said microprocessor means processing said electrical signals to determine the presence of said precipitation, and its type and intensity.

2. The laser precipitation sensor of claim 2 and wherein said housing means and said structure means are each hermetically sealed.

3. The laser precipitation sensor of claim 2 and further including lens means operatively associated with the housing means, and provided for collimating said light beam emitted from the light transmitting means.

4. The laser precipitation sensor of claim 3 and further including an apertured disc, operatively associated with the housing means and within the path of the deflected light beam, for passing a selected segment of the light beam to the light receiving means as it passes back into the housing means.

5. The laser precipitation sensor of claim 1 and wherein said microprocessor means processes the detected electrical signals using one of three different processes, a first corresponding to a temperature above a first select ambient temperature, a second corresponding to a temperature below a second select ambient temperature lower than said first select temperature, and a third corresponding to temperatures between said first and second select temperatures.

6. The laser precipitation sensor of claim 5 and further including EEprom means provided within the microprocessor means for receiving, storing, and altering the three different processes of the microprocessor means.

7. The laser precipitation sensor of claim 6 and further including random access memory means provided within the microprocessor means for storing accumulated data relating to the precipitation detected.

8. The laser precipitation sensor of claim 7 and further including read only memory means provided within the microprocessor means for storing various programs, subroutines, and directories which allow for the microprocessor means to process said electrical signals.

9. The laser precipitation sensor of claim 8 and wherein said microprocessor means further includes means for recording a count of the intensity of the precipitation interrupting the light beam.

10. The laser precipitation sensor of claim 1 and wherein said transmitted light beam is in the infrared spectrum.

* * * * *

UNITED STATES PATENT AND TRADEMARK OFFICE
CERTIFICATE OF CORRECTION

PATENT NO. : 5,298,750
DATED : March 29, 1994
INVENTOR(S) : Frank M. Rericha It is certified that error appears in the above-identified patent and that said Letters Patent is hereby corrected as shown below:

Col. 13, Claim 1, line 29, change "embodies" to ---embodied---.

Col. 14, Claim 2, line 9, change "claim 2" to ---claim 1---.

Signed and Sealed this

Nineteenth Day of July, 1994

Attest:

BRUCE LEHMAN

*Attesting Officer*        *Commissioner of Patents and Trademarks*